United States Patent [19]

Ladkani et al.

[11] Patent Number: 4,595,695

[45] Date of Patent: Jun. 17, 1986

[54] 1'-ETHOXYCARBONYLOXYETHYL ESTER OF VALPROIC ACID, ITS PREPARATION AND PHARMACEUTICAL COMPOSITIONS CONTAINING IT

[75] Inventors: David Ladkani, Jerusalem; Haim Yellin, Ramat-Gan; Ben Z. Weiner, Jerusalem, all of Israel

[73] Assignee: Teva Pharmaceutical Industries Ltd., Israel

[21] Appl. No.: 552,336

[22] Filed: Nov. 16, 1983

[30] Foreign Application Priority Data

Jan. 5, 1983 [IL] Israel ........................................ 67623

[51] Int. Cl.<sup>4</sup> ...................... A61K 31/265; C07C 69/00
[52] U.S. Cl. ...................................... 514/512; 558/276
[58] Field of Search ........................ 260/463; 424/301; 514/512

[56]  References Cited

U.S. PATENT DOCUMENTS

| 3,325,361 | 6/1967 | Meunier | 514/391 |
| 3,646,201 | 2/1972 | Kallianos et al. | 260/463 |
| 4,426,391 | 1/1984 | Alexander et al. | 260/463 |
| 4,483,867 | 11/1984 | Svahn et al. | 260/463 |
| 4,542,158 | 9/1985 | Dorn | 260/463 |

FOREIGN PATENT DOCUMENTS

| 1093068 | 1/1981 | Canada . |  |
| 0082404 | 6/1983 | European Pat. Off. | 260/463 |
| 0114720 | 1/1984 | European Pat. Off. | 260/463 |
| 0112130 | 6/1984 | European Pat. Off. | 260/463 |

OTHER PUBLICATIONS

Pisani et al., *Ther. Drug. Monitor*, vol. 3, pp. 297–301, (1981).
Musolino et al., *Acta Neurol.* vol. 2, pp. 107–113, (1980).
Reekers-Ketting et al. *Chemical Abstracts*, vol. 84: 83936t, (1976).
Gugler et al. *Chemical Abstracts*, vol. 92: 174011u (1980).
Levy, *Ther. Drug Mon.*, vol. 2, pp. 199–201, (1980).
Bodin et al. "Bacampicillin: A New Orally Well Absorbed Derivative of Ampicillin" in *Antimicrobial Agents & Chemotherapy* 8 (5) Nov. 1975 pp. 518–525.

*Primary Examiner*—Donald G. Daus
*Assistant Examiner*—Stephen M. Kapner
*Attorney, Agent, or Firm*—Steinberg & Raskin

[57]  ABSTRACT

1'-Ethoxycarbonyloxyethyl ester of di-n-propylacetic acid, also known as valproic acid. The novel compound is prepared by reacting valproic acid with 1-haloethyl ethyl carbonate. There are also provided pharmaceutical compositions for oral administration containing the said ester.

3 Claims, No Drawings

1'-ETHOXYCARBONYLOXYETHYL ESTER OF VALPROIC ACID, ITS PREPARATION AND PHARMACEUTICAL COMPOSITIONS CONTAINING IT

The present invention concerns the 1'-ethoxycarbonyloxyethyl ester of di-n-propylacetic acid also known as valproic acid.

Valproic acid (VPA) is a relatively new antiepileptic drug. It has the shortest elimination half life time of all the other commonly used antiepileptic agents, ranging between 6 to 17 hours. In combination therapy with other anti-epileptic drugs the half life time becomes even shorter than in a single therapy due to liver enzyme induction (R. Gugler and G. E. Von Unruh, Clin. Pharmacok. 5, 67 (1980)). This relatively short half life implies more fluctuations of VPA plasma concentration at steady states and even greater fluctuations in the free (unbound) plasma levels of the drug (R. H. Levy, Therapeutic Drug Monitoring 2, 199 (1980)). Due to its short half life time, VPA has to be administered to the patient three to five times a day.

VPA is pharmaceutically formulated into soft gelatin capsules or is supplied as sodium valproate in standard and enteric coated tablets, solutions and syrups. Despite the many brands of the above-mentioned formulations, it must still be administered 3-5 times a day. The dire need for a VPA sustained released dosage form for the epileptic patients and its environment is well realised (Antiepileptic Therapy, Advances in Drug monitoring, Raven Press, New York, 1979, p.253) as it would reduce the dosage, improve compliance and reduce the VPA plasma level fluctuation during chronic treatment, but so far no such successful dosage form is available for use.

In an attempt to prolong the effect of valproic acid, the concept of prodrug which will be biotransformed almost completely to valproic acid in a rate-limiting fashion has been tried, so far without success. In the literature there is a single report about an ester prodrug of valproic acid. This prodrug is 2-propylpentanol-di-n-propyl acetate. However, this ester has proved to be very toxic to animals and was not introduced for therapy (Reekers-Ketting et al., Pharm. Week. 110, 1232 (1975).

Valpromide-dipropylacetamide (VPD) which is used in several European countries as an antiepileptic and psychotic drug is not satisfactory. Although VPD might possess some psychotic or antiepileptic activity of its own after oral administration (Musolino et al., Acta Neurol. 2 , 107 (1980)), it has low bioavailability. VPD has a slower absorption than VPA, a fact which causes less fluctuation in VPA plasma levels during oral chronic treatment of VPA, but it still is far from being a satisfactory long-acting antiepileptic drug (Pisani et al., Ther. Drug Monitor; 3, 297 (1981)).

The present invention relates to a novel and useful 1'-ethoxycarbonyloxyethyl ester prodrug of valproic acid, a process for its production and of an anti-epileptic pharmaceutical preparation comprising such ester with less ulcerogenicity when administered orally than is valproic acid from which it is derived. The novel ester acts as a prodrug exhibiting characteristics of a slow release profile of the parent drug VPA, from which it is derived, and is suitable for the satisfactory control of the epileptic patient. It is sufficient to administer it twice or even once a day.

The novel compound according to the present invention is a 1'-ethoxycarbonyloxyethyl ester prodrug of an acid. Other such esters, serving as prodrugs are already in therapeutic use. For example 1'-ethoxycarbonyloxyethyl ester prodrugs of the penicillin series such as, for example, α-aminopenicillins and penicillin G are known.

It has also been found that the absorption of such esters from the intestinal tract is superior to the absorption of the corresponding free acids, which means that upon oral administration they yield higher blood concentrations than the corresponding free acid of α-aminopenicillin.

Usually the unionized form of a drug is absorbed more efficiently than its ionic species. In the case of valproic acid, the carboxylic group is significantly ionized at physiological pH. The result is that valproic acid is poorly absorbed through lipid-water membrane barriers, and in addition is irritating to the mucous membrane of the intestinal tract.

In spite of this state of the art and the need for an effective VPA prodrug, notwithstanding, no such prodrug has yet been produced. It is therefore the object of the present invention to provide such a prodrug.

In one of its aspects the invention concerns the novel compound 1'-ethoxycarbonyloxyethyl ester of valproic acid having the formula:

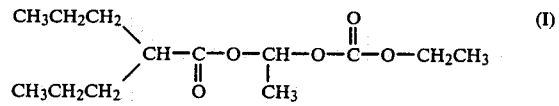

This novel compound is a liquid at room temperature and can readily be formulated into pharmaceutical compositions for oral administration, e.g. syrups and soft gelatin capsules, by methods well known to those skilled in the art.

The invention further provides pharmaceutical compositions for oral administration comprising 1'-ethoxycarbonyloxyethyl ester of valproic acid together with a pharmaceutically acceptable carrier.

Such compositions, when administered orally, produce a high degree of anti-epileptic activity and less side effects on the gastrointestinal tract, in comparison with valproic acid itself.

The invention also provides a process for the preparation of the novel compound of formula (I) comprising reacting valproic acid or a salt thereof with 1-haloethyl ethyl carbonate of the general formula:

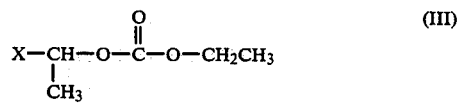

wherein X represents a halogen atom, preferably Cl or Br.

Most preferred for the synthesis is 1-bromoethyl ethyl carbonate, i.e. a compound of general formula (II) where X=Br. This compound has not yet been described in the literature. It can be produced by reacting diethyl carbonate with a brominating agent, for example bromine, N-bromosuccinimite, etc.

In the reaction, the compound of general formula (II) is used preferably in an amount of 1 mole or slightly more than 1 mole, per mole of the valproic acid. The reaction is performed usually in a solvent system consisting substantially of an aprotic inert organic solvent. In other words, the presence of a substantial amount of water or a protonic solvent such as alcohols in the reaction system is undesirable, because it induces hydrolysis of the compound of general formula (II). Examples of preferred aprotic inert organic solvent are dimethyl formamide, DMSO, acetone, acetonitrile, ethyl acetate and mixtures thereof.

When free valproic acid is used for the reaction, the reaction is preferably performed in the presence of a base. If, however, a salt of valproic acid is used, the reaction proceeds favourably in the absence of a base. Preferred bases to be present in the reaction system, when free valproic acid is used, include trialkylamines, such as triethylamine and metal hydrogen carbonates such as potassium hydrogen carbonate and sodium hydrogen carbonate and metal carbonates such as sodium and potassium carbonate. The same bases can also be used for the formation of a valproic acid salt for use in the reaction.

The reaction temperature is usually not higher than 56° C.

On oral administration, the ester of the invention is easily absorbed from the digestive tract, liberating valproic acid in vivo and maintaining a high valproic acid concentration in blood over long period of time.

This important advantage of the ester of the invention, is believed to be due to the fact that while this ester readily undergoes enzymatic hydrolysis in vivo to valproic acid prior to or during absorption processes, it seems to be somewhat resistant to hydrolysis in an aqueous acidic media.

Stability studies of this ester in plasma in vitro showed that the ester of this invention was transformed to valproic acid at room temperature.

Its stability half-life under the above conditions was 2.23 hours. The ester was quite stable at $-20°$ C. or after HCl was added to the plasma mixture. The stability half-life time in 0.01 N HCl at room temperature was 32.4 hours. All these half-life time calculations were done by assuming a first order linear kinetics of hydrolysis of the ester to valproic acid.

These results show that the ester of the present invention is hydrolyzed considerably more rapidly when subjected to the influence of hydrolytic enzymes, for instance, those present in blood plasma, and thus results in a release of the active valproic acid from the ester when this is absorbed from the intestinal tract.

Concentration of VPA after oral administration of the ester of this invention to five dogs are presented in the following Table I. Each plasma sample was assayed three times and the results presented in Table I are mean $\pm$S.D. of these analyses.

TABLE I

VPA plasma levels after oral administration of 1'-ethoxycarbonyloxyethyl ester to five dogs

| Sampling time (min) | Dog number 1 | 2 | 3 | 4 | 5 |
|---|---|---|---|---|---|
| | VPA plasma levels $\mu$g/ml | | | | |
| 15 | — | 11.20 ± 1.00 | 2.18 ± 0.26 | 1.93 ± 0.51 | 17.09 ± 1.47 |
| 30 | 2.69 ± 0.13 | 21.79 ± 0.77 | 10.69 ± 0.82 | 1.21 ± 0.07 | — |
| 45 | 5.71 ± 0.88 | 30.83 ± 1.49 | 15.56 ± 0.16 | — | 34.75 ± 0.25 |
| 60 | 10.01 ± 1.03 | 36.07 ± 1.05 | 22.17 ± 0.59 | — | 37.61 ± 2.74 |
| 75 | 14.75 ± 0.92 | 38.88 ± 1.82 | 10.85 ± 1.00 | — | 36.09 ± 0.98 |
| 90 | 17.01 ± 0.48 | 37.57 ± 1.09 | 10.35 ± 0.69 | 8.13 ± 0.18 | 39.12 ± 2.57 |
| 120 | 19.11 ± 1.78 | 31.86 ± 2.07 | 12.55 ± 0.12 | 12.24 ± 0.30 | 30.05 ± 0.79 |
| 150 | 17.70 ± 0.93 | 30.43 ± 1.32 | 7.22 ± 0.50 | 18.37 ± 3.16 | 25.21 ± 0.25 |
| 180 | 14.02 ± 0.49 | 22.85 ± 0.31 | 6.22 ± 0.76 | 15.13 ± 1.38 | 22.63 ± 1.43 |
| 210 | 11.03 ± 0.29 | 19.37 ± 1.67 | 4.43 ± 0.21 | — | 18.39 ± 0.96 |
| 240 | 8.62 ± 0.51 | 15.21 ± 0.04 | 3.91 ± 0.05 | 11.45 ± 1.42 | 15.71 ± 0.28 |
| 300 | 5.82 ± 1.05 | 11.31 ± 1.60 | 2.79 ± 0.24 | 7.34 ± 0.18 | 10.91 ± 1.11 |
| 360 | 6.29 ± 1.04 | 6.28 ± 0.61 | 2.59 ± 0.24 | 4.57 ± 0.71 | 7.94 ± 0.84 |
| 420 | 4.01 ± 0.86 | 8.68 ± 1.13 | 1.76 ± 0.10 | 3.87 ± 0.53 | 5.46 ± 0.41 |
| 480 | 4.44 ± 1.19 | 4.16 ± 0.74 | 1.48 ± 0.03 | 1.66 ± 0.30 | 3.64 ± 0.13 |
| 540 | 4.48 ± 0.67 | 2.96 ± 0.16 | 1.40 ± 0.01 | 1.63 ± 0.68 | 2.19 ± 0.43 |
| 600 | 1.18 ± 0.07 | 1.61 ± 0.10 | 1.36 ± 0.17 | 0.82 ± 0.39 | 1.03 ± 0.08 |
| 660 | — | — | 1.08 ± 0.00 | — | — |
| 720 | — | 0.48 ± 0.07 | — | — | 0.79 ± 0.12 |
| 780 | — | 0.52 ± 0.21 | — | — | — |
| 840 | — | — | — | — | — |
| 900 | — | — | — | — | — |

— Undetectable concentration of VPA.

The following Table II presents a summary of various pharmacokinetic parameters of VPA in dogs obtained after oral administration of the ester of this invention in comparison to those obtained after oral administration of VPA in acid form. All the pharmacokinetic parameters related to the distribution and elimination of VPA obtained after the administration of the two drug products were not significantly different (with the exception of V in dog number 1). The bioavailability of VPA after oral administration of the ester ranged between 62.9–100% (mean 79.01±14.09%; n=5). The absorption rate of VPA upon administration of the ester was two to five times slower than the one obtained upon administration of the free acid. More or less constant plasma levels of VPA were achieved between 30 to 240 minutes after the ester administration, with less than a two-fold difference between the maximal and minimal steady state levels.

TABLE II

Summary of the pharmacokinetic parameters obtained after oral administration of (I) and VPA as "DEPAKINE" (LABAZ) to five dogs.

| Pharmacokinetic Parameter | Dog 1 A 400 mg | Dog 1 B 400 mg | Dog 2 A 400 mg | Dog 2 B 400 mg | Dog 3 A 400 mg | Dog 3 B 400 mg | Dog 4 A 400 mg | Dog 4 B 400 mg | Dog 5 A 400 mg | Dog 5 B 400 mg |
|---|---|---|---|---|---|---|---|---|---|---|
| $k_e$ (min$^{-1}$) | $7.65 \cdot 10^{-3}$ | $5.5 \cdot 10^{-3}$ | $8.14 \cdot 10^{-3}$ | $6.5 \cdot 10^{-3}$ | $11.2 \cdot 10^{-3}$ | $121 \cdot 10^{-3}$ | $8.78 \cdot 10^{-3}$ | $6.5 \cdot 10^{-3}$ | $6.1 \cdot 10^{-2}$ | $5.8 \cdot 10^{-2}$ |
| $t_{\frac{1}{2}}$ elimin. (hr) | 1.44 | 2.10 | 1.44 | 1.78 | 1.05 | 0.95 | 1.28 | 1.78 | 1.93 | 1.93 |
| AUC $\left(\frac{mg \cdot min}{lit}\right)$ | 6854 | 4607.50 | 11,175 | 10,021.5 | 6507 | 4062 | 8583 | 4869 | 8422 | 8500 |
| V (lit) | 7.63 | 12.13 | 4.11 | 5.35 | 5.48 | 5.08 | 5.31 | 8.69 | 7.79 | 7.238 |
| CL (ml/min) | 58.36 | 66.70 | 35.79 | 34.76 | 61.41 | 61.45 | 46.60 | 56.49 | 47.49 | 42.71 |
| $k_a$ (min$^{-1}$) | 0.026 | 0.015 | 0.052 | 0.02 | 0.057 | 0.02 | 0.051 | 0.01 | 0.07 | 0.04 |
| F | 100 | 76.80 | 100 | 87.10 | 99 | 62.4 | 100 | 68.77 | 100 | 100 |
| t max obs (min) | 15 | 120 | 30 | 84 | 30 | 70 | 45 | 150 | 30 | 72 |
| Cb max obs (mg/L) | 36.4 | 19.00 | 60.57 | 39.00 | 58.96 | 22.20 | 46.60 | 18.5 | 79.5 | 37.50 |

A — VTA as sodium valproate ("DEPAKINE")
B — VPA as 1'-ethoxycarbonyloxyethyl ester
$k_e$ — Elimination rate constant
$k_a$ — Absorption rate constant
AUC — Area under the curve plasma conc. VS. time plot
F — Absolute bioavailability
V — Apparent volume of distribution = $\frac{CL}{k_e}$
t max — Time to reach peak plasma concentration
Cb max — Peak plasma concentration
CL — Total Body Clearance = $\frac{BD}{AUC}$
t max obs (min) = the observed time to reach peak plasma concentration
Cb max obs (mg/L) = the observed peak plasma concentration It is known that the VPA half-life time in man is three to eight times longer than in dog. Consequently it is expected that a single oral administration of the ester to man will produce prolonged pseudo steady state concentration and there will thus be less fluctuation in the VPA plasma concentration with the ester. Based on the prolonged absorption of VPA after administration of the ester, this new prodrug might be administered to epileptic patients twice or even once a day.

The compound of the present invention did not show any toxicity when it was administered orally to rats in doses of 20 and 100 mg/kg.

The invention is further illustrated by the following Examples to which it is not limited.

EXAMPLE 1

Production of 1-bromoethyl ethyl carbonate

A mixture of 195 g diethylcarbonate and 500 ml of 1,1,2-trichlorotrifluoroethane was irradiated externally by a 1.5 kw iodine-quartz lamp. The mixture soon refluxed by the heat evolved from the lamp. The temperature in the flask was 60° C. 79.0 g of 1,3-dibromo-5,5-dimethylimidazoline-2,4-dione was added in small portions during 6 hours. The mixture was irradiated and refluxed for another 20 minutes and cooled. Solids were removed by filtration. The solution was fractionally distilled first at atmospheric pressure and then under vacuum. 1-Bromoethyl ethyl carbonate was distilled at 91° C. at 20 mm Hg pressure. The fraction weighed 60 g and was shown to be 98% pure, by GC.

The following are physical data of 1-bromoethyl ethyl carbonate:
Boiling point at 60 mm Hg - 110°
Bromine content 40.6% (theoretical) 40.61%)
Density ($D_4^{20}$): 1 4244
Refractive index ($n_D^{20}$): 1.5395

NMR Spectrum: 1.4 ppm 3H triplet J=7 Hz 2.0 ppm 3H doublet J=6 Hz 4.25 ppm 2H quartet J=7 Hz 6.6 ppm 1H quartet J=6 Hz.

EXAMPLE 2

Preparation of 1'-ethoxycarbonyloxyethyl ester from sodium valproate

Anhydrous potassium carbonate (0.3 equivalent) was added to a solution of sodium valproate in acetone. To the mixture, 1.2 mole equivalents 1-bromoethyl ethyl carbonate was added and the mixture was heated for 3–4 hrs at reflux. The cooled mixture was poured into water and stirred for 1 hr at room temperature.

The organic phase was separated. The aqueous phase was washed with methylene chloride. The combined organic phases were washed with water and dried with MgSO$_4$. The pure oily product was obtained in 80% yield after evaporation of the methylene chloride.

IR (neat) 1745 and 1755 cm$^{-1}$ (s)

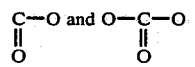

NMR, δ (CDCl ) 6.45 (1H, quartet, CH$_3$CH-O) 3.90 (2H, quartet, CH$_3$CHHD 2O) 2.10 (1H, quartet, CHCH$_2$CH$_2$CH$_3$)$_2$ 1.30 (3H, doublet, CH$_3$CHO) 0.80–1.20 (17H, CH$_3$CH$_2$O and n-propyl).

Anal. calcd. for C$_{13}$H$_{24}$O$_5$ (M.W. 260 1): C 59.96, H 9.30, Found: C 60.60, H 9.50.
$n_D^{25}$: 1.4205
$D_{20}$ 1.05.

EXAMPLE 3

Preparation of 1'-ethoxycarbonyloxy ethyl ester from sodium valproate with valproic acid as solvent Sodium valproate (0.1 mole) and 1.2 mole equivalents 1-bromoethyl ethyl carbonate (BEC) were added to 15 ml/valproic acid. The mixture was heated for 1 hr at 120° C. The crude reaction mixture was analysed by G.C. after adding methylene chloride and filtering. 96% conversion of BEC to the desired product was achieved after ½ hrs.

EXAMPLE 4

Preparation of 1'-ethoxycarbonyloxyethyl ester from valproic acid in acetone

Anhydrous potassium carbonate (0.3 equivalents) was added to a solution of valproic acid (0.1 mole) in acetone. To the mixture, 1.2 mole equivalents 1-bromoethyl ethyl carbonate were added and the mixture was heated for 2-3 hours at reflux. The cooled mixture was poured into water and stirred for 1 hour at room temperature. The organic phase was separated. The aqueous phase was extracted with methylene chloride and the organic phase was dried with MgSO₄. G.C. analysis showed that the crude reaction mixture contains 95% of the desired product.

We claim:

1. Valproic acid 1'-ethoxycarbonyloxyethyl ester of the formula:

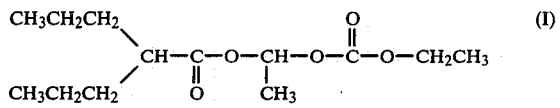

2. Method of effecting anti-epileptic action, which comprises administering to a patient requiring the same an anti-epileptic effective amount of the compound of claim 1.

3. An anti-epileptic pharmaceutical composition for oral administration comprising an anti-epileptic effective amount of valproic acid 1'-ethoxycarbonyloxyethyl ester together with a pharmaceutically acceptable carrier.